United States Patent
Pruitt et al.

(10) Patent No.: US 9,052,442 B2
(45) Date of Patent: Jun. 9, 2015

(54) METHOD FOR APPLYING A COATING ONTO A SILICONE HYDROGEL LENS

(75) Inventors: John Dallas Pruitt, Suwanee, GA (US);
Lynn Cook Winterton, Alpharetta, GA (US); Sai Ramamurthy Kumar, Johns Creek, GA (US); Dawn A. Smith, Duluth, GA (US)

(73) Assignee: Novartis AG, Basel (CH)

( * ) Notice: Subject to any disclaimer, the term of this patent is extended or adjusted under 35 U.S.C. 154(b) by 2255 days.

(21) Appl. No.: 11/978,336

(22) Filed: Oct. 29, 2007

(65) Prior Publication Data
US 2008/0100796 A1    May 1, 2008

Related U.S. Application Data

(60) Provisional application No. 60/863,407, filed on Oct. 30, 2006.

(51) Int. Cl.
| | | |
|---|---|---|
| A61L 12/14 | (2006.01) | |
| G02C 7/04 | (2006.01) | |
| B05D 5/06 | (2006.01) | |
| G02B 1/10 | (2006.01) | |
| A61L 12/04 | (2006.01) | |
| B29D 11/00 | (2006.01) | |
| C08J 7/04 | (2006.01) | |
| G02B 1/04 | (2006.01) | |

(52) U.S. Cl.
CPC . *G02B 1/10* (2013.01); *A61L 12/14* (2013.01); *G02C 7/04* (2013.01); *A61L 12/04* (2013.01); *B29D 11/00038* (2013.01); *B29D 11/00865* (2013.01); *C08J 7/04* (2013.01); *C08J 2383/00* (2013.01); *G02B 1/043* (2013.01)

(58) Field of Classification Search
CPC .................................. A61L 12/14; G02C 7/04
See application file for complete search history.

(56) References Cited

U.S. PATENT DOCUMENTS

| | | | | |
|---|---|---|---|---|
| 4,168,112 A |  | 9/1979 | Ellis et al. | 351/160 |
| 4,321,261 A |  | 3/1982 | Ellis et al. | 424/180 |
| 4,560,491 A | * | 12/1985 | Sherman | 514/275 |
| 4,941,997 A |  | 7/1990 | Decher et al. | 252/586 |
| 4,973,429 A |  | 11/1990 | Decher et al. | 252/587 |
| 5,068,318 A |  | 11/1991 | Decher et al. | 534/573 |
| 5,208,111 A |  | 5/1993 | Decher et al. | 428/420 |
| 5,509,899 A |  | 4/1996 | Fan et al. | 604/96 |
| 5,518,767 A |  | 5/1996 | Rubner et al. | 427/259 |
| 5,529,727 A |  | 6/1996 | LaBombard et al. | 264/1.36 |
| 5,529,787 A |  | 6/1996 | Merrill et al. | 264/1.36 |
| 5,536,573 A |  | 7/1996 | Rubner et al. | 428/378 |
| 5,700,559 A |  | 12/1997 | Sheu et al. | 428/319.7 |
| 5,856,370 A | * | 1/1999 | Chmelir | 521/128 |
| 5,882,687 A |  | 3/1999 | Park et al. | 424/682 |
| 6,011,082 A |  | 1/2000 | Wang et al. | 523/107 |
| 6,087,415 A |  | 7/2000 | Vanderlaan et al. | 524/105 |
| 6,428,839 B1 |  | 8/2002 | Kunzler et al. | 427/2.1 |
| 6,451,871 B1 |  | 9/2002 | Winterton et al. | 523/106 |
| 6,531,432 B2 |  | 3/2003 | Molock et al. | 510/112 |
| 6,589,665 B2 |  | 7/2003 | Chabrecek et al. | 428/520 |
| 6,689,480 B2 |  | 2/2004 | Shimoyama et al. | 428/451 |
| 6,699,435 B2 |  | 3/2004 | Salpekar et al. | 422/40 |
| 6,719,929 B2 |  | 4/2004 | Winterton et al. | 264/1.7 |
| 6,793,973 B2 |  | 9/2004 | Winterton et al. | 427/393.5 |
| 6,811,805 B2 |  | 11/2004 | Gilliard et al. | 427/2.1 |
| 6,815,074 B2 |  | 11/2004 | Aguado et al. | 428/447 |
| 6,827,966 B2 |  | 12/2004 | Qiu et al. | 427/2.24 |
| 6,858,248 B2 |  | 2/2005 | Qiu et al. | 427/2.24 |
| 6,893,685 B2 |  | 5/2005 | Qiu et al. | 427/407 |
| 6,896,926 B2 | * | 5/2005 | Qiu et al. | 427/2.31 |
| 6,926,965 B2 |  | 8/2005 | Qiu et al. | 428/411.1 |
| 6,940,580 B2 |  | 9/2005 | Winterton et al. | 352/160 |
| 7,022,379 B2 |  | 4/2006 | Winterton et al. | 427/307 |
| 7,211,149 B2 |  | 5/2007 | Qiu et al. | 118/429 |
| 2001/0045676 A1 |  | 11/2001 | Winterton et al. | 264/2.5 |
| 2001/0048975 A1 |  | 12/2001 | Winterton et al. | 427/412.1 |
| 2002/0006493 A1 |  | 1/2002 | Chabrecek et al. | 428/64.1 |
| 2002/0086160 A1 |  | 7/2002 | Qiu et al. | 428/413 |
| 2002/0182316 A1 |  | 12/2002 | Gilliard et al. | 427/162 |
| 2003/0008154 A1 |  | 1/2003 | Aguado et al. | 428/447 |
| 2003/0012872 A1 |  | 1/2003 | Qiu et al. | 427/162 |
| 2003/0039742 A1 |  | 2/2003 | Qiu et al. | 427/2.1 |
| 2003/0052424 A1 |  | 3/2003 | Turner et al. | 264/1.32 |
| 2003/0109390 A1 |  | 6/2003 | Salpekar et al. | 510/112 |
| 2003/0117579 A1 |  | 6/2003 | Morris et al. | 351/200 |

(Continued)

FOREIGN PATENT DOCUMENTS

| | | |
|---|---|---|
| EP | 0 032 443 | 5/1985 |
| EP | 0 032 443 | 6/1985 |

(Continued)

OTHER PUBLICATIONS

EPO Standard Search Report.
PCT International Search Report—Mail Date Dec. 9, 2003.
PCT International Search Report—Mail Date Mar. 12, 2008.
Written Opinion of the International Searching Authority.
Yoo, Lee and Rubner, "Investigations of New Self-Assembled MultiLayer Thin Films Based on Alternately Adsorbed Layers of Polyelectrolytes and Functional Dye Molecules", 1996, pp. 395-400.
Yoo & Rubner, "Layer-By-Layer Modification of Surfaces Through The Use of Self Assembled Monolayers of Polyions", 1995, pp. 2568-2570.
Ferreira and Rubner, "Molecular Level Processing of Conjugated Polymers. 1. Layer by Layer Manipulation of Conjugated Polyions", 1995, pp. 7107-7114.

(Continued)

*Primary Examiner* — Michael G Hartley
*Assistant Examiner* — Lance Rider
(74) *Attorney, Agent, or Firm* — Jian Zhou

(57) ABSTRACT

The invention provides a cost-effective and in-situ method for applying an LbL coating onto a silicone hydrogel contact lens directly in a lens package. The resultant silicone hydrogel contact lens has a coating with good hydrophilicity, intactness and durability and also can be used directly from the lens package by a patient without washing and/or rising. In addition, the invention provides a packaging solution for in-situ coating of a silicone hydrogel contact lens in a lens package and an ophthalmic lens product.

10 Claims, No Drawings

(56) References Cited

U.S. PATENT DOCUMENTS

| | | | |
|---|---|---|---|
| 2003/0125498 A1 | 7/2003 | McCabe et al. | 528/25 |
| 2003/0134132 A1 | 7/2003 | Winterton et al. | 428/451 |
| 2003/1117579 | 7/2003 | Morris et al. | 351/200 |
| 2003/0162862 A1 | 8/2003 | McCabe et al. | 523/106 |
| 2003/0219909 A1 | 11/2003 | Lally et al. | 547/529 |
| 2004/0135967 A1 | 7/2004 | Carney et al. | 351/159 |
| 2005/0008676 A1 | 1/2005 | Qiu et al. | 424/429 |

FOREIGN PATENT DOCUMENTS

| | | |
|---|---|---|
| EP | 0 138 385 | 4/1990 |
| EP | 0 995 762 | 4/2000 |
| GB | 2 102 070 | 1/1983 |
| JP | 1-158412 | 6/1989 |
| JP | 5-318118 | 12/1993 |
| JP | 07256844 | 10/1995 |
| WO | WO 95/00618 | 1/1995 |
| WO | WO 95/02251 | 1/1995 |
| WO | WO 95/20407 | 8/1995 |
| WO | WO 96/18498 | 6/1996 |
| WO | WO 96/31792 | 10/1996 |
| WO | WO 96/37241 | 11/1996 |
| WO | WO 97/44687 | 11/1997 |
| WO | 98/42487 | 10/1998 |
| WO | WO 99/35520 | 7/1999 |
| WO | WO 01/57118 | 8/2001 |
| WO | WO 01/92924 | 12/2001 |
| WO | WO 02/16974 | 2/2002 |
| WO | WO 02/097481 | 12/2002 |
| WO | WO 03/066714 | 8/2003 |
| WO | WO 2005/025991 | 3/2005 |
| WO | WO 2006/038080 | 4/2006 |

OTHER PUBLICATIONS

Fou and Rubner, "Molecular Level Processing of Conjugated Polymers. 2. Layer by Layer Manipulation of In-Situ Polymerized p-Type Doped Conducting Polymers", 1995, pp. 7115-7120.

Cheung, Stockton & Rubner, "Molecular Level Processing of Conjugated Polymers. 3. Layer by Layer Manipulation of Polyaniline via Electrostatic Interactions", 1997, pp. 2712-2716.

Cheung, Fou, Ferreira and Rubner, "Molecular Self Assembly of Conducting Polymers: A New Layer by Layer Thin Film Deposition Process", pp. 757-758.

Vargo, Calvert, Wynne, Avlyanov, MacDiarmid, and Rubner, "Patterned Polymer multilayer Fabrication by Controlled Adhesion of Polyelectrolytes to Plasma modified Fluoropolymer Surfaces", 1995, pp. 169-174.

Winterton, Qiu and Lally, "Coating for Biomedical Devices", Abstracts of Papers, 223$^{rd}$ ACS National Meeting, Orlando, FL, US, Apr. 7-11, 2002, Coll-392 Publisher; American Chemical Society, Washington, DC.

Translation of Japanese Office Action dtd Jan. 8, 2013 in JP 2009-535407.

Decher, Lehr, Lowack, Lvov & Schmitt, "New Nanocomposite Films for Biosensors: layer by Layer adsorbed films of polyelectrolytes, proteins or DNA", 1994, pp. 677-684.

Sukhorukov, Mohwald, Decher and Lvov, "Assembly of Polyelectrolyte Multilayer films by consecutively alternating adsorption of Polynucleotides and Polycations", 1996, pp. 220-223.

Uchida, Kunitake, and Kajiyama, "Blood Compatibility—Surface Characteristic Relationships of a Langmuir-Blodgett Film COmposed of an Anionic Amphiphile-Polycation COmplex", 1994, pp. 199-211.

Onitsuka, Fou, Ferreira, Hsieh, and Rubner, "Enhancement of Light Emitting Diodes Based on Self-Assembled Heterostructures of Poly(p-PHenylene Vinylene)", 1996, pp. 4067-4071.

Yoo, Lee and Rybner, "Investigations of New Self-Assembled MultiLayer Thin Films Based on Alternately Adsorbed Layers of Polyelectrolytes and Functional Dye Molecules", 1996, pp. 395-400.

Yoo, Wu, Lee and Rubner, "New Electro-Active Self-Assembled MultiLayer Thin Films Based on Alternately Adsorbed Layers of Polyelectrolytes and Functional Dye Molecules", 1997, pp. 1425-1426.

Yoo & rubner, "Layer-By-Layer Modification of Surfaces Through the USe of Self Assembled Monolayers of Polyions", 1995, pp. 2568-174.

Ferreira and Rubner, "Molecular Level Processing of Conjugated Polymers. Layer by Layer Manipulation of Conjugated Polyions", 1995, pp. 7107-7114.

Fou and Rubner, "Molecular Level Processing of Conjugated Polymers. Layer by Layer Manipulation of In-Situ Polymerized p-Type Doped Conducting Polymers", 1995, pp. 7115-7120.

Cheung, Stockton & Rubner, "Molecular Level Processing of Conjugated Polymers. Layer by Layer Manipulation of Polyanilene via Electrostatic Interactions", 1995, pp. 2712-2716.

Cheung, Fou, Ferreira and Rubner, "Molecular Self Assembly of Conducting Polymers: A New Layer by Layer Thin Film Deposition Process", pp. 757-758, 1993.

Vargo, Clavert, Wynne, Avlyanov, MacDiarmid, and Rubner, "Patterned Polymer multilayer Fabrication by Controlled Adhesion of Polyelectrolytes to Plasma modified Fluoropolymer Surfaces", 1996, pp. 169-174.

Hirotusuga, Yasuda, "Biocompatibility of Nonofilm-Encapsulated Silicone and Silicone-Hydrogel Contact Lenses", 2006, pp. 121-138.

Winterton, Lynn, et al., Coating for Biomedical Devices, Abstracts of Papers, 223$^{rd}$ ACS National Meeting, Orlando, FL, Apr. 7-11, 2002, coll-392, publisher; American Chemical Society, Washington, DC.

\* cited by examiner

METHOD FOR APPLYING A COATING ONTO A SILICONE HYDROGEL LENS

This application claims the benefit under 35 U.S.C. §119(e) of U.S. provisional patent application Ser. No. 60/863,407 filed Oct. 30, 2006, herein incorporated by reference in its entirety.

The present invention generally relates to a method for applying a coating of hydrophilic polymers onto silicone hydrogel contact lenses to improve hydrophilicity and lubricity. In addition, the present invention provides a silicone hydrogel contact lens having a hydrophilic coating with a good coverage and durability.

BACKGROUND OF THE INVENTION

In recent years, soft silicone hydrogel contact lenses, for example, Focus NIGHT & DAY™ and O2OPTIX™ (CIBA VISION), and PureVision™ (Bausch & Lomb) become more and more popular because of their high oxygen permeability and comfort. "Soft" contact lenses conform closely to the shape of the eye, so oxygen cannot easily circumvent the lens. Soft contact lenses must allow oxygen from the surrounding air (i.e., oxygen) to reach the cornea because the cornea does not receive oxygen from the blood supply like other tissue. If sufficient oxygen does not reach the cornea, corneal swelling occurs. Extended periods of oxygen deprivation cause the undesirable growth of blood vessels in the cornea. By having high oxygen permeability, a silicone hydrogel contact lens allows sufficient oxygen permeate through the lens to the cornea and to have minimal adverse effects on corneal health.

However, a silicone hydrogel material typically has a surface or at least some areas of its surface which is hydrophobic (non-wettable). Lipids or proteins from the ocular environment can be adsorbed onto hydrophobic surface or surface areas of a silicone hydrogel contact lens. The hydrophobic surface or surface areas of a silicone hydrogel contact lens may cause it be adhered to the eye. Thus, a silicone hydrogel contact lens will generally require a surface modification to increase surface hydrophilicity.

A known method for modifying the hydrophilicity of a relatively hydrophobic contact lens material is a layer-by-layer (LbL) polyionic (or polyelectrolyte) material deposition technique (see for example, U.S. Pat. Nos. 6,451,871, 6,717,929, 6,793,973, 6,884,457, 6,896,926, 6,926,965, 6,940,580). LbL coatings may provide high hydrophilicity and lubricity to contact lenses and thereby enhance wearer's comfort and/or ocular health. Although this technique can provide a cost effective process for rendering a silicone hydrogel material wettable, it may require relatively long time and laborious steps to apply an LbL hydrophilic coating which can impart hydrophilicity and lubricity to a silicone hydrogel contact lens. Moreover, an LbL coating process generally is carried out at very low pH (e.g., below pH 4) or at very high pH (e.g., above pH 9), and as such, one or more additional post-coating processes are needed to neutralize pH before each coated lens can be placed in a packaging saline at a pH of about 7 in a package. Such additional post-coating processes may decrease the production efficiency and increase the production cost.

Therefore, there is still a need for methods of efficiently applying a hydrophilic coating to a silicone hydrogel contact lens.

SUMMARY OF THE INVENTION

The invention, in one aspect, provides a method of applying a hydrophilic coating onto a silicone hydrogel contact lens, the method of invention comprising: (a) placing the contact lens in a lens package containing a packaging solution, wherein the packaging solution comprises a polyionic material and at least one hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of less than about 4.0 or larger than about 9.5, wherein the hydrolysable-at-autoclave material is present in the packaging solution in an amount sufficient to impart a final neutral pH to the packaging solution after the package with the contact lens therein is autoclaved; and (b) autoclaving said package with the contact lens and the packaging solution therein, thereby forming a hydrophilic coating on the contact lens immersed in the packaging solution with the final neutral pH in the package, wherein the coating has a hydrophilicity characterized by an averaged water contact angle of about 80 degrees or less.

In another aspect, the invention provides a lens packaging solution for storing a silicone hydrogel contact lens in a lens package. The packaging solution of the invention comprises a polyionic material and an hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of lower than about 4.0 or higher than about 9.5, wherein the hydrolysable-at-autoclave material is present in the packaging solution in an amount sufficient to impart a final neutral pH to the packaging solution after the packaging solution is autoclaved, wherein the packaging solution is characterized by its capability of being served as an in-situ coating solution during autoclave process of the package with the silicone hydrogel contact lens and the lens packaging solution therein to form a hydrophilic coating onto a silicone hydrogel contact lens without prior surface treatment and posterior pH adjustment, wherein the hydrophilic coating is not covalently attached to the silicone hydrogel contact lens and has a hydrophilicity characterized by an averaged water contact angle of about 80 degrees or less and by a good coating durability characterized by surviving a digital rubbing test.

In a further aspect, the invention provides an ophthalmic product comprising a pre-sterilized and sealed lens package which includes: a lens packaging solution comprising a polyionic material and an hydrolysable-at-autoclave material; and a silicone hydrogel contact lens without prior surface treatment and immersed in the lens packaging solution, wherein the polyionic material includes (i) a polymer having a hydrophobic backbone and multiple charged or ionizable pendant groups, (ii) a chitosan, or (iii) a combination thereof, wherein the packaging solution has an initial pH of lower than about 4.0 or higher than about 9.5, wherein the hydrolysable-at-autoclave material is present in the packaging solution in an amount sufficient to impart a final neutral pH to the packaging solution after the packaging solution is autoclaved.

The invention, in still a further aspect, provides a method of providing a hydrogel contact lens an increased hydrophilicity, the method of invention comprising: (a) placing the contact lens in a lens package containing a packaging solution, wherein the packaging solution comprises a polyionic material and at least one hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of less than about 4.0 or larger than about 9.5, wherein the hydrolysable-at-autoclave material is present in the packaging solution in an amount sufficient to impart a final neutral pH to the packaging solution after the package with the contact lens therein is autoclaved; and (b) autoclaving said package with the contact lens and the packaging solution therein, thereby providing the packaging solution the final neutral pH in the package and providing the contact lens the increased hydrophilicity.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

"Hydrophilic," as used herein, describes a material or portion thereof that will more readily associate with water than with lipids.

A "monomer" means a low molecular weight compound that includes an actinically-crosslinkable group and can be polymerized actinically or thermally. Low molecular weight typically means average molecular weights less than 700 Daltons.

An "actinically-crosslinkable group" refers to a group which can react with another group of same type or different type to form a covalent linkage upon actinic irradiation. Examples of actinically-crosslinkable groups include without limitation ethylenically unsaturated groups, thiol groups, ene-containing groups. Ethylenically unsaturated groups can undergo free-radical chain reaction upon actinic irradiation. Thiol groups (—SH) and ene-containing groups can participate in thiol-ene step-growth radical polymerization as described in a commonly-owned copending U.S. patent application No. 60/869,812 filed Dec. 13, 2006 (entitled "PRODUCTION OF OPHTHALMIC DEVICES BASED ON PHOTO-INDUCED STEP GROWTH POLYMERIZATION", herein incorporated in reference in its entirety.

The term "olefinically unsaturated group" or "ethylenically unsaturated group" is employed herein in a broad sense and is intended to encompass any groups containing at least one >C=C< group. Exemplary ethylenically unsaturated groups include without limitation acryloyl, methacryloyl, allyl, vinyl, styrenyl, or other C=C containing groups.

As used herein, "actinically" in reference to curing or polymerizing of a polymerizable composition or material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

A "ene-containing group" is a mono-valent or divalent radical contains a carbon-carbon double which is not directly linked to a carbonyl group (—CO—), nitrogen atom, or oxygen atom and is defined by any one of formula (I)-(III)

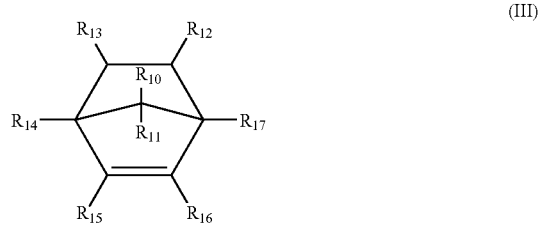

in which $R_1$ is hydrogen, or $C_1$-$C_{10}$ alkyl; $R_2$ and $R_3$ independent of each other are hydrogen, $C_1$-$C_{10}$ alkene divalent radical, $C_1$-$C_{10}$ alkyl, or —$(R_{18})_a$—$(X_1)_b$—$R_{19}$ in which $R_{18}$ is $C_1$-$C_{10}$ alkene divalent radical, $X_1$ is an ether linkage (—O—), a urethane linkage (—N), a urea linkage, an ester linkage, an amid linkage, or carbonyl, $R_{19}$ is hydrogen, a single bond, amino group, carboxylic group, hydroxyl group, carbonyl group, $C_1$-$C_{12}$ aminoalkyl group, $C_1$-$C_{18}$ alkylaminoalkyl group, $C_1$-$C_{18}$ carboxyalkyl group, $C_1$-$C_{18}$ hydroxyalkyl group, $C_1$-$C_{18}$ alkylalkoxy group, $C_1$-$C_{12}$ aminoalkoxy group, $C_1$-$C_{18}$ alkylaminoalkoxy group, $C_1$-$C_{18}$ carboxyalkoxy group, or $C_1$-$C_{18}$ hydroxyalkoxy group, a and b independent of each other is zero or 1, provided that only one of $R_2$ and $R_3$ is a divalent radical; $R_4$-$R_9$, independent of each other, are hydrogen, $C_1$-$C_{10}$ alkene divalent radical, $C_1$-$C_{10}$ alkyl, or —$(R_{18})_a$—$(X_1)_b$—$R_{19}$, provided that only one or two of $R_4$-$R_9$ are divalent radicals; n and m independent of each other are integer number from 0 to 9, provided that the sum of n and m is an integer number from 2 to 9; $R_{10}$-$R_{17}$, independent of each other, are hydrogen, $C_1$-$C_{10}$ alkene divalent radical, $C_1$-$C_{10}$ alkyl, or —$(R_{18})_a$—$(X_1)_b$—$R_{19}$, provided that only one or two of $R_{10}$-$R_{17}$ are divalent radicals.

A "vinylic monomer", as used herein, refers to a monomer that has an ethylenically unsaturated group and can be polymerized actinically or thermally.

A "hydrophilic vinylic monomer", as used herein, refers to a vinylic monomer which as a homopolymer typically yields a polymer that can absorb at least 10 percent by weight water.

A "hydrophobic vinylic monomer", as used herein, refers to a vinylic monomer which as a homopolymer typically yields a polymer that can absorb less than 10 percent by weight of water.

A "macromer" refers to a medium and high molecular weight compound which includes one or more actinically-crosslinkable group and can be polymerized and/or crosslinked. Medium and high molecular weight typically means average molecular weights greater than 700 Daltons. In accordance with the invention, an actinically-polymerizable macromer can be a macromer with one or more ethylenically unsaturated groups or with two or more thiol or ene-containing groups, which can participate in either free radical chain growth polymerization or thiol-ene step-growth radical polymerization.

A "prepolymer" refers to a starting polymer which contains actinically crosslinkable groups and can be cured (e.g., crosslinked) actinically to obtain a crosslinked polymer having a molecular weight much higher than the starting polymer.

A "silicone-containing prepolymer" refers to a prepolymer which contains silicone and can be crosslinked actinically to obtain a crosslinked polymer having a molecular weight much higher than the starting polymer.

A "polymer" means a material formed by polymerizing/crosslinking one or more monomers.

A "backbone" of a polymer refers to the principle chain in a polymer molecule.

As used herein, the term "multiple" refers to three or more.

"Surface modification" or "surface treatment", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, mold-transfer coating process disclosed in U.S. Pat. No. 6,719,929 (herein incorporated by reference in its entirety), the incorporation of wetting agents into a lens formulation for making contact lenses proposed in U.S. Pat. Nos. 6,367,929 and 6,822,016 (herein incorporated by references in their entireties), reinforced mold-transfer coating disclosed in U.S. Patent Application No. 60/811,949 (herein incorporated by reference in its entirety), and LbL coating. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to a contact lens and is obtained through a layer-by-layer ("LbL") deposition of polyionic (or charged) and/or non-charged materials. An LbL coating can be composed of one or more layers.

As used herein, a "polyionic material" refers to a polymeric material that has a plurality of charged groups or ionizable groups. Polyionic materials include both polycationic (having positive charges) and polyanionic (having negative charges) materials.

The term "bilayer" is employed herein in a broad sense and is intended to encompass: a coating structure formed on a contact lens by alternatively applying, in no particular order, one layer of a first polyionic material (or charged material) and subsequently one layer of a second polyionic material (or charged material) having charges opposite of the charges of the first polyionic material (or the charged material); or a coating structure formed on a contact lens by alternatively applying, in no particular order, one layer of a first charged polymeric material and one layer of a non-charged polymeric material or a second charged polymeric material. It should be understood that the layers of the first and second coating materials (described above) may be intertwined with each other in the bilayer.

Formation of an LbL coating on a contact lens or mold half may be accomplished in a number of ways, for example, as described in U.S. Pat. Nos. 6,451,871, 6,719,929, 6,793,973, 6,811,805, 6,896,926 (herein incorporated by references in their entireties).

"Post-curing surface treatment", in reference to a silicone hydrogel material or a soft contact lens, means a surface treatment process that is performed after the formation (curing) of the hydrogel material or the soft contact lens in a mold.

A "hydrophilic surface" in reference to a silicone hydrogel material or a contact lens means that the silicone hydrogel material or the contact lens has a surface hydrophilicity characterized by having an averaged water contact angle of about 90 degrees or less, preferably about 80 degrees or less, more preferably about 70 degrees or less, more preferably about 60 degrees or less.

An "average contact angle" refers to a water contact angle (measured by Sessile Drop method), which is obtained by averaging measurements of at least three individual contact lenses.

As used herein, "increased surface hydrophilicity" or "increased hydrophilicity" in reference to a contact lens means that the contact lens autoclaved in a packaging solution of the invention has a smaller averaged (water) contact angle relative to that of a control contact lens autoclaved in a buffered saline packaging solution without a polyionic material and at least one hydrolysable-at-autoclave material, wherein all contact lenses are made of the same core material.

The term "intactness" in reference to a coating on a silicone hydrogel contact lens is intended to describe the extent to which the contact lens can be stained by Sudan Black in a Sudan Black staining test described in Example 1. Good intactness of the coating on a silicone hydrogel contact lens means that there is practically no Sudan Black staining of the contact lens.

The term "durability" in reference to a coating on a silicone hydrogel contact lens is intended to describe that the coating on the silicone hydrogel contact lens can survive a digital rubbing test.

As used herein, "surviving a digital rubbing test" in reference to a coating on a contact lens means that after digitally rubbing the lens with Solo-Care® (CIBA Vision) or an equivalent, there is no noticeable increase in staining area on the lens relative to the staining of a lens of same without rubbing, as described in Example 1. In accordance with the invention, a silicone hydrogel contact lens of the invention has a coating that is capable of surviving preferably at least 5, more preferably at least 10, even more preferably at least 20 consecutive digital rubbing tests.

As used herein, the term "a neutral pH" in reference to a solution means that the pH of the solution is from about 6.0 to about 8.0.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3\ oxygen)/(cm^2)(sec)(mm^2\ Hg)] \times 10^{-9}$$

The intrinsic "oxygen permeability", Dk, of a lens material does not depend on lens thickness. Intrinsic oxygen permeability is the rate at which oxygen will pass through a material. Oxygen permeability is conventionally expressed in units of barrers, where "barrer" is defined as:

$$[(cm^3\ oxygen)(mm)/(cm^2)(sec)(mm^2\ Hg)] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm $$\left(\frac{90 \times 10^{-10}}{0.09} = 100 \times 10^{-9}\right)$$

(oxygen transmissibility barrers/mm). In accordance with the invention, a high oxygen permeability in reference to a material or a contact lens characterized by apparent oxygen permeability of at least 40 barrers or larger measured with a sample (film or lens) of 100 microns in thickness according to a coulometric method described in Examples.

The "ion permeability" through a lens correlates with both the Ionoflux Diffusion Coefficient and the Ionoton Ion Permeability Coefficient.

The Ionoflux Diffusion Coefficient, D, is determined by applying Fick's law as follows:

$$D = -n'/(A \times dc/dx)$$

where n'=rate of ion transport [mol/min]
A=area of lens exposed [mm$^2$]
D=Ionoflux Diffusion Coefficient [mm$^2$/min]
dc=concentration difference [mol/L]
dx=thickness of lens [mm]

The Ionoton Ion Permeability Coefficient, P, is then determined in accordance with the following equation:

$$\ln(1-2C(t)/C(0)) = -2APt/Vd$$

where: C(t)=concentration of sodium ions at time t in the receiving cell
C(0)=initial concentration of sodium ions in donor cell
A=membrane area, i.e., lens area exposed to cells
V=volume of cell compartment (3.0 ml)
d=average lens thickness in the area exposed
P=permeability coefficient An Ionoflux Diffusion Coefficient, D, of greater than about $1.5 \times 10^{-6}$ mm$^2$/min is preferred, while greater than about $2.6 \times 10^{-6}$ mm$^2$/min is more preferred and greater than about $6.4 \times 10^{-6}$ mm$^2$/min is most preferred.

It is known that on-eye movement of the lens is required to ensure good tear exchange, and ultimately, to ensure good corneal health. Ion permeability is one of the predictors of on-eye movement, because the permeability of ions is believed to be directly proportional to the permeability of water.

In general, the invention is directed to a cost-effective surface treatment method for making silicone hydrogel contact lenses with durable hydrophilic coatings. The invention is partly based on the discovery that when some materials (i.e., hydrolysable-at-autoclave materials), for example, such as, urea, ammonium carbamate, ester (e.g., polyvinyl acetate), or anhydride, is added into a lens packaging solution, they can be hydrolyzed during autoclave process (i.e., sterilization of the lens packages). The hydrolysis products of such material can change the pH of the packaging solution from a low or high value to a neutral value (e.g., around pH=7). As such, the initial (prior to autoclave) and final (posterior autoclave) pH values of a lens packaging solution can be controlled as one desires.

The invention is also partly based on the discovery that an LbL coating can be applied onto a silicone hydrogel contact lens, in situ, directly in a lens package containing a lens packaging solution including a hydrolysable-at-autoclave material and under optimal coating conditions for forming an LbL coating with good hydrophilicity, intactness and durability on a silicone hydrogel contact lens. Although the inventors do not wish to be bound by any particular theory, it is believed that through hydrophobic-hydrophobic interaction, the hydrophobic backbone of a coating material may strongly interact with the hydrophobic surface areas of a silicone hydrogel contact lens to anchor the coating material onto the lens surface. At extreme pH, e.g., at low pH, the ionizable groups of a polyanionic material may not be ionized and the hydrophobic backbone of the polyanionic material may have the strongest interaction with the hydrophobic surface areas of a silicone hydrogel contact lens. It is also believed that at a higher coating temperature, molecules of a coating material might be able to be in more close contact with the hydrophobic surface areas of the lens and then "trapped" there once the temperature drops. Another theory is that small amounts of the surface would exhibit opposite charges to the polyionic material added to the packaging solution. This charge-charge interaction may also play an important anchor for the resultant coating.

Contact lenses, which are hydrated and packaged in solution, must be sterilized. Sterilization of the hydrated lenses during manufacturing and packaging is typically accomplished by autoclaving. The autoclaving process involves heating the packaging of a contact lens to a temperature of about 121° C. for approximately 20-30 minutes under pressure. Since contact lenses in the lens packages typically need to be sterilized by autoclave at about 121° C., an in situ LbL coating of a silicone hydrogel contact lens can be carried out at high temperature and at extreme pH (at least for the first several minutes of autoclave). It is discovered that, by incorporating in the lens packaging solution a hydrolysable-at-autoclave material which can produce base or acid during hydrolysis process, the final pH of the packaging solution can be automatically adjusted to a neutral pH value after autoclave. By using the method of the invention, the coating process is combined with the sterilization step (autoclave) in the manufacturing of silicone hydrogel contact lenses. No prior surface treatment is needed. The resultant contact lenses not only can have a high surface hydrophilicity and good intactness and durability, but also can be used directly from the lens package by a patient without washing and/or rising because of the neutral pH and adequate tonicity of the packaging solution.

As used herein, an "in situ LbL coating process" is intended to describe a process in which an LbL coating is applied onto a contact lens directly in a lens package which is supplied to a customer. Any lens packages known to a person skilled in the art can be used in the invention.

The invention, in one aspect, provides a method of applying a hydrophilic coating onto a silicone hydrogel contact lens, the method of invention comprising: (a) placing the contact lens in a lens package containing a packaging solution, wherein the packaging solution comprises a polyionic material and at least one hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of less than about 4.0 or larger than about 9.5, wherein the hydrolysable-at-autoclave material is present in the packaging solution in an amount sufficient to impart a final neutral pH to the packaging solution after the package with the contact lens therein is autoclaved; and (b) autoclaving said package with the contact lens and the packaging solution therein, thereby forming a hydrophilic coating on the contact lens immersed in the packaging solution with the final neutral pH in the package, wherein the coating has a hydrophilicity characterized by an averaged water contact angle of about 80 degrees or less.

In accordance with the invention, the packaging solution is an aqueous solution which is ophthalmically safe. The term "ophthalmically safe" with respect to an aqueous solution for sterilizing and storing contact lenses is meant that a contact lens stored in the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

A variety of packages can be used to store contact lenses, including for example, vials, blister packages or equivalents. In particular, so-called blister packages are widely used for the storage and dispensing of the contact lenses. Typically, the blister package for storing and dispensing a contact lens includes an injection-molded or thermoformed plastic base portion incorporating a molded cavity which is surrounded by an outstanding planar flange about the rim of the cavity. The plastic base portion is made of plastic material. A flexible cover sheet is adhered to the surface of the flange so as to seal or enclose the cavity in a generally liquid-tight mode. Within the cavity of the base portion, a contact lens is immersed in a sterile aqueous solution, such as an isotonic saline solution.

The base portion may be formed from a variety of plastic materials, but is preferably transparent to allow the user to inspect the lens without opening the storage package. The plastic material should be capable of being sterilized at 120° C. without substantial loss of its physical properties of dimensional stability, warpage, and shrinkage. The plastic material should have low water and vapor permeability to prevent the evaporation and loss of the lens care solution. The plastic material should not be permeable to bacteria and oxygen in order to avoid contamination and to keep the efficacy of the solution. Preferably, plastic materials should have a high strength and a high tolerance, in view of the cost and efficiency in manufacturing the base portion and easiness in handling the material.

Examples of plastic materials include without limitation fluoro-resin, polyamide, polyacrylate, polyethylene, nylons, olefin co-polymers (e.g., copolymers of polypropylene and polyethylene), polyethylene terephthalate, poly vinyl chloride, non-crystalline polyolefin, polycarbonate, polysulfone, polybutylene terephthalate, polypropylene, polymethyl pentene, polyesters, rubbers, urethanes, and the like. These materials are adopted solely or alternatively in a composite body or a laminar structure. The plastic material used to make the base is preferably polypropylene.

The base portion is preferably prepared by injection molding or thermoforming and may be in any desired forms.

The cavity of the base portion may be suitably designed and sized with no limitation to receive the lens and the sufficient quantity of sterile preserving solution to completely submerge the lens. The cavity may have a variety of shapes in plane view, including a circular shape, a polygonal shape, an ellipsoidal shape, a heart shape, and the like. The surface of the cavity may be desirably shaped depending upon a specific configuration, size and the like of an ophthalmic lens to be received in the cavity. For instance, the surface of the cavity may have a hemisphere (concave) shape.

In accordance with the present invention, at least the surface of the cavity of a base portion is modified by surface treatment. The surface treatment can be performed by a variety of methods, including without limitation plasma treatment, plasma coating, corona discharge, LbL coating, flame treatment and acid surface etching treatment. Preferably, the surface treatment is corona discharge, plasma treatment, or LbL coating.

Typically, the base comprises a flange portion extending about the cavity containing a soft contact lens in a sterile packaging solution, so as to ensure that at least the cavity is appropriately sealed by a flexible cover sheet.

The cover sheet may be a single film or alternatively a multi-layered film, and any film may be adopted as the cover sheet as long as the film is capable of being sealed to the container base by bonding, welding or other similar methods. The flexible cover sheet may be formed of a variety of water-impermeable materials and may have a variety of thicknesses. The sheet must be sufficiently flexible to enable the user to easily remove the sheet from the base portion. The cover sheet is preferably a laminate material preferably comprising a metal foil layer and at least one, preferably two polymer layers, e.g. polypropylene, coating the foil. The preferred foil is aluminum. Preferably, the sheet is formed from a metal (e.g., aluminum) foil or foil composite.

The cover sheet may be printed with information regarding the contact lens contained in the package or with other information for the end user or the dealer. The base may be affixed to the flexible cover sheet by a number of methods. However, the strength of the bond between the base and sheet should not be excessive, i.e., the user should be able to easily and quickly separate the sheet from the base. For example, the cover sheet can be sealed to the base or flange thereof by means of temperature or ultrasonic treatment or by another appropriate adhesion method.

It should be understood that a plurality of base parts, e.g., four base parts, advantageously form one unit, so that handling of the base parts in the manufacturing process is simplified.

Any materials, which can be hydrolyzed during autoclave to produce an acidic or base material, can be used as hydrolysable-at-autoclave material in the invention. Examples of preferred as hydrolysable-at-autoclave materials include without limitation urea, ammonium carbamate, water-soluble polyvinyl acetates, esters, anhydrides, and the like. Urea and ammonium carbamate can be hydrolyzed during autoclave to form ammonium as hydrolysis product to increase a solution's pH. Polyvinyl acetates, esters and anhydrides can be hydrolyzed during autoclave to form acid as hydrolysis product to decrease a solution's pH. The amount of the hydrolysable-at-autoclave material in the packaging solution should be sufficient to impart a final neutral pH (i.e., from about 6.0 to about 8.0) to the packaging solution after autoclave.

In accordance with the invention, a polyionic material for forming LbL coating has a hydrophobic backbone. Although the inventors do not wish to be bound by any particular theory, it is believed that through hydrophobic-hydrophobic interaction, the hydrophobic backbone of a coating material may strongly interact with the hydrophobic surface areas of a silicone hydrogel contact lens to anchor the coating material onto the lens surface.

The polyionic materials that may be employed in the present invention include polyanionic and polycationic polymers with a hydrophobic backbone and charged or ionizable pendant groups.

Examples of suitable polyanionic polymers include, without limitation a linear polyacrylic acid (PAA), a branched polyacrylic acid, a polymethacrylic acid (PMA), a copolymer of acrylic acid, a copolymer of methacrylic acid, a maleic or fumaric acid copolymer, a poly(styrenesulfonic acid) (PSS). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone. A preferred polyanionic polymer with a hydrophobic backbone is a polymer containing carboxyl groups (—COOH). It is believed that carboxyl groups can be protonated at a pH of about 1 to about 3. A more preferred polyanionic polymer with a hydrophobic backbone is a linear or branched polyacrylic acid or an acrylic acid copolymer. A more preferred anionic polymer is a linear or branched polyacrylic acid. A branched polyacrylic acid in this context is to be understood to be a polyacrylic acid obtainable by polymerizing acrylic acid in the presence of suitable (minor) amounts of a di- or multi-vinyl compound.

Examples of polycationic polymers with a hydrophobic backbone include, without limitation, a polyallylamine (PAH) homopolymer, a polyallylamine (PAH) copolymer, a polyethyleneimine (PEI), a polyvinylamine homopolymer, a polyvinylamine copolymer, a poly(vinylbenzyl-tri-$C_1$-$C_4$-alkylammonium salt), poly(vinylpyridinium salt), polyquat. The above mentioned polymers comprise in each case the free amine, a suitable salt thereof as well as any quaternized form, if not specified otherwise. The above mentioned copolymers preferably comprises units derived from hydrophilic monomers, e.g., such as acrylamide, methacrylamide, N,N-dimethyl acrylamide, N-vinylpyrrolidone and the like. A polyallylamine (PAH) copolymer more preferably comprises modifier units of formula (1)

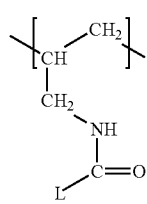

(1)

wherein L is $C_2$-$C_6$-alkyl, which is substituted by two or more same, or different substituents selected from the group consisting of hydroxy, $C_2$-$C_5$-alkanoyloxy and $C_2$-$C_5$-alkylamino-carbonyloxy. Examples of such polyallylamine copolymers are disclosed in WO 00/31150 (herein incorporated by reference in its entirety).

In a preferred embodiment, the packaging solution has an initial pH of less than about 4.0, preferably, less than about 3, even more preferably about 2.5 or less and comprises a polyanionic material having a hydrophobic backbone and pendant ionizable groups, and urea or ammonium carbamate as hydrolysable-at-autoclave material. Where the packaging solution has a low pH, the pendant ionizable groups of the polyanionic can be prevented from being ionized (i.e., becoming charged groups) and the hydrophobic-hydrophobic interactions between the hydrophobic backbone of the polyanionic material and the hydrophobic surface areas of a silicone hydrogel contact lens can be increased.

In another preferred embodiment, the packaging solution has an initial pH of less than about 4.0, preferably, less than about 3, even more preferably about 2.5 or less and comprises: a polyanionic material having a hydrophobic backbone and pendant ionizable groups; a polycationic material; and urea or ammonium carbamate as hydrolysable-at-autoclave material. Preferably, the concentration of the polyanionic material is higher than that of the polycationic material.

In another preferred embodiment, the packaging solution has an initial pH of less than about 4.0, preferably, less than about 3, even more preferably about 2.5 or less and comprises: a polyanionic material having a hydrophobic backbone and pendant ionizable groups; a non-charged hydrophilic material with a hydrophobic backbone; and urea or ammonium carbamate as hydrolysable-at-autoclave material.

Any suitable non-charged hydrophilic polymers with a hydrophobic backbone can be used in the invention. They are preferably polyvinyl alcohols (PVAs), more preferably a homopolymer of a vinyl lactam, a copolymer of at least one vinyl lactam in the presence or in the absence of one or more hydrophilic vinylic comonomers, or mixtures thereof.

PVA is a highly biocompatible material used widely in ophthalmic products, especially wetting drops or artificial tears for ocular comfort (e.g., HypoTears™, etc.). PVAs of all kinds, for example those with low, medium or high polyvinyl acetate contents may be employed. Polyvinyl alcohols employed in the present invention are known and are commercially available, for example under the brand name Mowiol® from KSE (Kuraray Specialties Europe).

In accordance with the invention, the vinyl lactam has a structure of formula (IV)

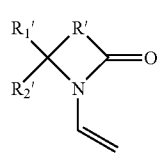

(IV)

wherein R' is an alkylene di-radical having from 2 to 8 carbon atoms; $R_1'$ is hydrogen, alkyl, aryl, aralkyl or alkaryl, preferably hydrogen or lower alkyl having up to 7 carbon atoms, and, more preferably, up to 4 carbon atoms, such as, for example, methyl, ethyl or propyl; aryl having up to 10 carbon atoms, and also aralkyl or alkaryl having up to 14 carbon atoms; and $R_2'$ is hydrogen or lower alkyl having up to 7 carob atoms and, more preferably, up to 4 carbon atoms, such as, for example, methyl, ethyl or propyl.

A preferred non-charged hydrophilic polymer is a copolymer derived from a vinyl lactam which is a heterocyclic monomer of formula (IV) containing from 4 to 6 carbon atoms in the heterocyclic ring, or a mixture thereof. A more preferred non-charged hydrophilic polymer is a copolymer derived from a vinyl lactam which is a heterocyclic monomer of formula (IV) containing 4 carbon atoms in the heterocyclic ring, or a mixture thereof. An even more preferred non-charged hydrophilic polymer is a copolymer derived from a vinyl lactam which is a heterocyclic monomer of formula (IV) containing 4 carbon atoms in the heterocyclic ring and wherein $R_1'$ and $R_2'$ are each independently of the other hydrogen or lower alkyl, or a mixture thereof. A most preferred non-charged hydrophilic polymer is polyvinylpyrrolidone (PVP).

In another preferred embodiment, the packaging solution has an initial pH of less than about 4.0, preferably, less than about 3, even more preferably about 2.5 or less and comprises a chitosan and urea or ammonium carbamate as hydrolysable-at-autoclave material.

Chitosan is generally referred to products of deacetylation of chitin, poly[β-(1→4)-2-acetamido-2-deoxy-D-glucopyranose]. Chitosan is soluble in dilute acid solution (i.e., at low pH) because of protonation of free amine groups of chitosan, but insoluble in water or a solution having a pH near neutrality.

In another preferred embodiment, the packaging solution has an initial pH of less than about 4.0, preferably, less than about 3, even more preferably about 2.5 or less and comprises: a polyanionic material having a hydrophobic backbone and pendant carboxylic (—COOH) groups; a chitosan; and urea or ammonium carbamate as hydrolysable-at-autoclave material. Preferably, the concentration of the polyanionic material is higher than that of the chitosan. It is believed that at a low pH, the pendant carboxylic groups of the polyanionic can be prevented from being ionized (i.e., becoming charged groups) while free amine groups of chitosan is protonated (become charged). Because of strong hydrophobic-hydrophobic interactions between the hydrophobic backbone of the polyanionic material and the hydrophobic surface areas of a silicone hydrogel contact lens, the polyanionic material is believed to be deposited first onto the silicone hydrogel contact lens to form a layer and then chitosan is bound to the layer of polyanionc material on the lens.

In another preferred embodiment, the packaging solution has an initial pH of higher than about 9.0, preferably higher than about 10.0, and comprises a polycationic material having a hydrophobic backbone and pendant charged or ionizable groups and polyvinyl acetate as hydrolysable-at-autoclave material.

In another preferred embodiment, the packaging solution has an initial pH of higher than about 9.0, preferably higher than about 10.0, and comprises: a polycationic material having a hydrophobic backbone and pendant charged or ionizable groups; a polyanionic material; and water-soluble polyvinyl acetate as hydrolysable-at-autoclave material.

In another preferred embodiment, the packaging solution has an initial pH of higher than about 9.0, preferably higher than about 10.0, and comprises: a polycationic material having a hydrophobic backbone and pendant charged or ionizable groups; a non-charged hydrophilic material with a hydrophobic backbone; and water-soluble polyvinyl acetate as hydrolysable-at-autoclave material.

In accordance with the present invention, packaging solutions can be prepared in a variety of ways. Preferably, a packaging solution can be formed by dissolving a coating material (e.g., polyionic materials and optionally non-charged hydrophilic materials) and a hydrolysable-at-autoclave material in water. The concentration of the coating material in a solution can generally vary depending on the particular materials being utilized, the desired coating thickness, and a number of other factors. It may be typical to formulate a relatively dilute aqueous solution of a coating material. For example, a coating material concentration can be between about 0.0001% to about 0.25% by weight, between about 0.005% to about 0.10% by weight, or between about 0.01% to about 0.05% by weight.

In order to alter various characteristics of the coating, such as thickness, the molecular weight of the coating materials can be varied. In particular, as the molecular weight is increased, the coating thickness generally increases.

The packaging solution preferably contains a buffering agent. The buffering agents maintain the pH preferably in the desired range, for example, in a physiologically acceptable range of from about 6.3 to about 7.8, preferably between 6.5 to 7.6, even more preferably between 6.8 to 7.4. Any known, physiologically compatible buffering agents can be used. Suitable buffering agents as a constituent of the packaging solution according to the invention are known to the person skilled in the art. Examples are: boric acid, borates, e.g. sodium borate, citric acid, citrates, e.g. potassium citrate, bicarbonates, e.g. sodium bicarbonate, phosphate buffers (e.g. $Na_2HPO_4$, $NaH_2PO_4$, $Na_2HPO_4$, and $KH_2PO_4$, TRIS (tris(hydroxymethyl)aminomethane), 2-bis(2-hydroxyethyl) amino-2-(hydroxymethyl)-1,3-propanediol, bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino) ethanesulfonic acid), MOPS 3-[N-morpholino]-propanesulfonic acid, PIPES (piperazine-N,N'-bis(2-ethanesulfonic acid), TES (N-[Tris(hydroxymethyl)methyl]-2-aminoethanesulfonic acid), and salts thereof. The amount of each buffer agent is that amount necessary to be effective in achieving a desired pH. Typically, it is present in an amount of from 0.001% to 2%, preferably from 0.01% to 1%; most preferably from about 0.05% to about 0.30% by weight.

The packaging solution are formulated in such a way that they are isotonic with the lachrymal fluid. A solution which is isotonic with the lachrymal fluid is generally understood to be a solution whose concentration corresponds to the concentration of a 0.9% sodium chloride solution.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol, sorbitol, xylitol, mannitol, propylene glycol, polyethylene glycol (PEG) with a molecular weight of about 400 Da or less, and mixtures thereof. The tonicity of the solution is typically adjusted to be in the range from about 200 to about 450 milliosmol (mOsm), preferably from about 200 to 450 mOsm, preferably from about 250 to 350 mOsm.

A packaging solution may further comprise a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, and the like. A mucin-like material may be used to alleviate dry eye syndrome. The mucin-like material preferably is present in effective amounts. Exemplary hydrophilic polymers include, but are not limited to, polyvinylalcohols (PVAs), polyamides, polyimides, polylactone, a homopolymer or copolymer of a vinyl lactam in the presence or in the absence of one or more hydrophilic vinylic comonomers (poly(vinylpyrrolidone) (PVP)), a homopolymer of acrylamide or methacrylamide, a high molecular weight PEG (with a molecular weight of greater than about 50000 Da, a copolymer of acrylamide or methacrylamide with one or more hydrophilic vinylic monomers, mixtures thereof.

In accordance with the invention, the packaging solutions of the present invention optionally can contain a viscosity enhancing agent which is preferably a cellulose ether, more preferably methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. Even more preferably, a cellulose ether is hydroxyethyl cellulose (HEC), hydroxypropylmethyl cellulose (HPMC), or a mixture thereof. The cellulose ether is present in the solution in an amount of from about 0.01% to about 5% by weight, preferably from about 0.05% to about 3% by weight, even more preferably from about 0.1% to about 1% by weight, based on the total amount of the solution.

In another aspect, the invention provides a lens packaging solution for storing a silicone hydrogel contact lens in a lens package. The packaging solution of the invention comprises a polyionic material and an hydrolysable-at-autoclave material, wherein the polyionic material includes a hydrophobic backbone and multiple charged or ionizable pendant groups, wherein the packaging solution has an initial pH of lower than about 4.0 or higher than about 9.5, wherein the hydrolysable-at-autoclave material is present in the packaging solution in an amount sufficient to impart a final neutral pH to the packaging solution after the packaging solution is autoclaved, wherein the packaging solution is characterized by its capability of being served as an in-situ coating solution during autoclave process of the package with the silicone hydrogel contact lens and the lens packaging solution therein to form a hydrophilic coating onto a silicone hydrogel contact lens without prior surface treatment and posterior pH adjustment, wherein the hydrophilic coating is not covalently attached to the silicone hydrogel contact lens and has a hydrophilicity characterized by an averaged water contact angle of about 80 degrees or less and by a good coating durability characterized by surviving a digital rubbing test.

Above described various embodiments and preferred embodiments of packages, coating techniques, coating materials, and coating temperature can be used in this aspect of the invention.

In a further aspect, the invention provides an ophthalmic product comprising a pre-sterilized and sealed lens package which includes: a lens packaging solution comprising a polyionic material and an hydrolysable-at-autoclave material; and a silicone hydrogel contact lens without prior surface treatment and immersed in the lens packaging solution, wherein the polyionic material includes (i) a polymer having a hydrophobic backbone and multiple charged or ionizable pendant groups, (ii) a chitosan, or (iii) a combination thereof, wherein the packaging solution has an initial pH of lower than about 4.0 or higher than about 9.5, wherein the hydrolysable-at-autoclave material is present in the packaging solution in an amount sufficient to impart a final neutral pH to the packaging solution after the packaging solution is autoclaved.

As used herein, the term "a pre-sterilized and sealed lens package" is intended to describe a sealed lens package which has not been subjected to sterilization by autoclave.

The silicone hydrogel contact lens comprises a core silicone hydrogel material which is the copolymerization product of a silicone hydrogel lens-forming material. The silicone-hydrogel lens-forming material comprises at least one member selected from the group consisting of a silicone-containing vinylic monomer, a silicone-containing macromer with ethylenically unsaturated groups, a crosslinkable silicone-containing prepolymer, and mixtures thereof.

Silicone hydrogel contact lenses can be produced according to any known methods. Examples of lens-producing methods include without limitation lathing, cast molding, spin casting, and combinations thereof.

The silicone hydrogel contact lens after autoclave preferably has one of the following properties: an oxygen permeability of at least 40 barrers, an ion permeability characterized by having an Ionoflux Diffusion Coefficient of greater than about $1.5 \times 10^{-6}$ mm$^2$/min, wettable surface characterized by an averaged water contact angle of 80 degrees or less and a good coating durability characterized by surviving a digital rubbing test or repeated autoclave test.

A surface treatment process of the invention can also be used to increased surface hydrophilicity of non-silicone hydrogel contact lens. The invention, in still a further aspect, provides a method of providing a hydrogel contact lens an increased hydrophilicity, the method of invention comprising: (a) placing the contact lens in a lens package containing a packaging solution, wherein the packaging solution comprises a polyionic material and at least one hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of less than about 4.0 or larger than about 9.5, wherein the hydrolysable-at-autoclave material is present in the packaging solution in an amount sufficient to impart a final neutral pH to the packaging solution after the package with the contact lens therein is autoclaved; and (b) autoclaving said package with the contact lens and the packaging solution therein, thereby providing the packaging solution the final neutral pH in the package and providing the contact lens the increased hydrophilicity.

Above described various embodiments and preferred embodiments of packaging solution and lens packages can be used in this aspect of the invention.

The previous disclosure will enable one having ordinary skill in the art to practice the invention. In order to better enable the reader to understand specific embodiments and the advantages thereof, reference to the following examples is suggested.

EXAMPLE 1

Surface Hydrophilicity (Wettability) Tests

Water contact angle on a contact lens is a general measure of the surface hydrophilicity (or wettability) of the contact lens. In particular, a low water contact angle corresponds to more hydrophilic surface. Average contact angles (Sessile Drop) of contact lenses are measured using a VCA 2500 XE contact angle measurement device from AST, Inc., located in Boston, Mass. This equipment is capable of measuring advancing or receding contact angles or sessile (static) contact angles. The measurements are performed on fully hydrated contact lenses and immediately after blot-drying.

Coating Intactness Tests

The intactness of a coating on the surface of a contact lens can be tested according to Sudan Black stain test as follow. Contact lenses with a coating (an LbL coating, a plasma coating, or any other coatings) are dipped into a Sudan Black dye solution (Sudan Black in vitamin E oil). Sudan Black dye is hydrophobic and has a great tendency to be adsorbed by a hydrophobic material or onto a hydrophobic lens surface or hydrophobic spots on a partially coated surface of a hydrophobic lens (e.g., silicone hydrogel contact lens). If the coating on a hydrophobic lens is intact, no staining spots should be observed on or in the lens. All of the lenses under test are fully hydrated.

Coating Durability Tests

The lenses are digitally rubbed with Solo-Care® multi-purpose lens care solution for 30 times and then rinsed with saline. The above procedure is repeated for a given times, e.g., from 1 to 30 times, (i.e., number of consecutive digital rubbing tests which imitate cleaning and soaking cycles). The lenses are then subjected to Sudan Black test (i.e., coating intactness test described above) to examine whether the coating is still intact. To survive digital rubbing test, there is no significantly increased staining spots (e.g., staining spots covering no more than about 5% of the total lens surface). Water contact angles are measured to determine the coating durability.

Oxygen Permeability Measurements.

The oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 $cm^3$/min., while a nitrogen stream is passed on the opposite side of the lens at a rate of about 10 to 20 $cm^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app} = Jt/(P_{oxygen})$$

where J=oxygen flux [microliters $O_2$/$cm^2$-minute]
$P_{oxygen}$=($P_{measured}$−$P_{water}$ vapor)=(% $O_2$ in air stream)[mm Hg]=partial pressure of oxygen in the air stream
$P_{measured}$=barometric pressure (mm Hg)
$P_{water}$ vapor=0 mm Hg at 34° C. (in a dry cell) (mm Hg)
$P_{water}$ vapor=40 mm Hg at 34° C. (in a wet cell) (mm Hg)
t=average thickness of the lens over the exposed test area (mm)
where $Dk_{app}$ is expressed in units of barrers.

The oxygen transmissibility (Dk/t) of the material may be calculated by dividing the oxygen permeability ($Dk_{app}$) by the average thickness (t) of the lens.

Ion Permeability Measurements

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of $0.314 \times 10^{-3}$ $mm^2$/minute.

EXAMPLE 2

Six buffers are prepared to investigate the effect of urea levels on the final pH of the buffer after autoclave. The buffers are adjusted to an initial pH of 2.5 with HCl (1 N). The buffers are placed in crimped vials and autoclaved for 45 minutes at 121° C. The buffer formulations and the post-autoclave pH are shown in Table 1.

TABLE 1

| Citric Acid Monohydrate | Glycerol | Trometh-amine | Polyacrylic acid | Urea | post-autoclave pH |
|---|---|---|---|---|---|
| 0.21% | 2% | 0.30% | 0.01% | 0.05% | 3.87 |
| 0.21% | 2% | 0.30% | 0.01% | 0.10% | 5.15 |
| 0.21% | 2% | 0.30% | 0.01% | 0.30% | 6.80 |
| 0.21% | 2% | 0.00% | 0.01% | 0.05% | 3.76 |
| 0.21% | 2% | 0.00% | 0.01% | 0.10% | 5.25 |
| 0.21% | 2% | 0.00% | 0.01% | 0.30% | 6.54 |

EXAMPLE 3

Eight buffers are prepared to have varying levels of urea and tromethamine (Tris). The buffers are adjusted with HCl (1 N) to an initial pH of 2.5. Polyurea contact lenses, which are prepared as described in Example 4 of a co-pending U.S. Patent Application Publication No. 2007-0195261A1 (herein incorporated by reference in its entirety), are packaged in the buffers and autoclaved for 45 minutes at 121° C. The lenses appears more wettable than un-coated control lenses. The pH of the buffers is measured immediately after autoclaving and 45 minutes after opening the packages to allow the buffer to be equilibrated with the atmosphere. The pH increases after the packages are allowed to equilibrate with the atmosphere. It is believed that this phenomenon is likely due to loss of dissolved $CO_2$ in the buffers. The post-autoclave and equilibrium pH are shown in Table 2.

TABLE 2

| Citric Acid Monohydrate (%) | Glycerol (%) | Tris (%) | PAA (%) | Urea (%) | post-autoclave pH | equilibrium pH |
|---|---|---|---|---|---|---|
| 0.21 | 2.0 | 0.07 | 0.025 | 0.20 | 6.25 | 6.78 |
| 0.21 | 1.9 | 0.07 | 0.025 | 0.25 | 6.66 | 7.37 |
| 0.21 | 1.8 | 0.07 | 0.025 | 0.28 | 6.80 | 7.50 |
| 0.21 | 1.7 | 0.07 | 0.025 | 0.30 | 6.97 | 7.57 |
| 0.21 | 1.8 | 0.29 | 0.025 | 0.20 | 6.73 | 7.25 |
| 0.21 | 1.7 | 0.29 | 0.025 | 0.25 | 6.77 | 7.32 |
| 0.21 | 1.6 | 0.29 | 0.025 | 0.28 | 6.96 | 7.47 |
| 0.21 | 1.5 | 0.29 | 0.025 | 0.30 | 7.03 | 7.50 |

EXAMPLE 4

Six buffers are prepared and adjusted to a pH of 2.0 with HCl (1 N). Uncoated Lotrafilcon B lenses are packaged in the buffers and autoclaved. After being autoclaved the lenses appear to be coated and are fully wettable in PBS.

The six buffer samples are also autoclaved in lens packaging blisters and then placed in an oven at 45° C. and the pH of the packaging saline is monitored over time. The formulations and resulting pH data are shown in Table 3 and indicate that the pH appears to have leveled off after approximately 19 days.

TABLE 3

| Citric Acid Monohydrate | Glycerol (%) | TRIS (%) | PAA (%) | Urea (%) | pH Day 6 | Day 12 | Day 19 | Day 34 |
|---|---|---|---|---|---|---|---|---|
| 0.21% | 1.9 | 0.07 | 0.025 | 0.25 | 6.16 | 6.45 | 6.47 | |
| 0.21% | 1.8 | 0.07 | 0.025 | 0.28 | 6.38 | 6.72 | 6.97 | |
| 0.21% | 1.7 | 0.07 | 0.025 | 0.30 | 6.78 | 7.31 | 7.53 | |
| 0.21% | 1.7 | 0.29 | 0.025 | 0.25 | 6.37 | 6.55 | 6.77 | 6.75 |
| 0.21% | 1.6 | 0.29 | 0.025 | 0.28 | 6.71 | 7.05 | 7.18 | 7.16 |
| 0.21% | 1.5 | 0.29 | 0.025 | 0.30 | 7.06 | 7.38 | 7.51 | 7.49 |

EXAMPLE 5

A buffer containing 250 ppm PAA, 0.21% citric acid monohydrate, 1.6% glycerol, 0.291% tromethamine, and 0.275% urea is adjusted to a pH of 2.0 with 1-normal HCl. Uncoated lotrafilcon B lenses are packaged in the buffer and autoclaved for 30 minutes at 121° C. The lenses appeared highly wettable and had a sessile drop (water) contact angle of 35 degrees. The lenses show no staining with sudan black right out of the package and after five cleaning cycles (manually rubbed lenses with Aquify® followed by rinsing with Clear Care).

EXAMPLE 6

Three buffers are prepared with sodium chloride instead of glycerol as a tonicity adjusting agent as shown in Table 4. HCl (1 N) and NaOH (1 N) are used to adjust the pH to 2.0 and uncoated lotrafilcon B lenses are packaged in the buffers and autoclaved. After being autoclaved the lenses are highly wettable and show no staining with sudan black.

TABLE 4

| Phosphoric acid | NaCl | Tromethamine | Polyacrylic acid | Urea | equilibrium pH |
|---|---|---|---|---|---|
| 0.25% | 0.5% | 0.30% | 0.025% | 0.20% | 6.49 |
| 0.25% | 0.5% | 0.30% | 0.025% | 0.25% | 6.76 |
| 0.25% | 0.5% | 0.30% | 0.025% | 0.30% | 6.93 |

EXAMPLE 7

Buffers are prepared containing 0.21% citric acid monohydrate, 1.6% glycerol, 0.291% tromethamine, 0.275% urea and various polyionic materials in order to compare the coating effectiveness of the different polyionic materials. All buffers are adjusted to a pH of 2.0 and uncoated lotrafilcon B lenses are packaged in the buffers and autoclaved. After autoclaving the lenses are stained for 15 minutes in sudan black and then rinsed with water. Results are shown in Table 5.

TABLE 5

| Polyionic material | Sudan Black Staining | Contact Angle |
|---|---|---|
| Uncoated control | Stained | 108 degrees |
| Polymethacrylic acid | Slight staining (much less than control) | 89 degrees |
| Poly(90% acrylic acid, 10% acrylamide) | No staining | 62 degrees |
| Poly(10% acrylic acid, 90% acrylamide) | Stained similar to control | 91 degrees |
| Polystyrene sulfonate | Stained similar to control | 92 degrees |
| Polyacrylic acid + 20 ppm povidone | Very slightly stained | 102 degrees |

The best results (no staining and lower water contact angle) can be obtained with poly(90% acrylic acid, 10% acrylamide), like polyacrylic acid in Example 6. Even though the data with polymethacrylic acid show a fairly high contact angle and slight staining, the resultant lenses feel very lubricious. Where polyionic material is Poly(10% acrylic acid, 90% acrylamide) or Polystyrene sulfonate, the contact angle is around 90 degrees compared to control lenses, indicating that lenses are coated with the polyionic material. However, Sudan black may still be able to bind to the hydrophobic backbone of the polyionic material. When polyacrylic acid+ povidone are used to coat lenses, contact angle is high and there is slightly staining. These results probably is due to the hydrophilic portion of the PVP binding to the acrylic acid groups and leaving the hydrophobic backbone exposed on the exterior of the lens due to formation of complexes between PVP.

EXAMPLE 8

A buffer containing 0.05% PAA, 0.14% sodium phosphate monobasic, 2.0% glycerol, and 0.2% urea is prepared and adjusted to a pH of 2.5 with 1 N HCl solution. Uncoated lotrafilcon B lenses are packaged in the buffer and autoclaved for 30 minutes at 121° C. The lenses are wettable and have a sessile drop (water) contact angle of 30-50 degrees.

What is claimed is:
1. A method for applying a hydrophilic coating onto a silicone hydrogel contact lens, comprising the steps of:
   (a) placing the contact lens in a lens package containing a packaging solution, thereby forming an LbL coating on the contact lens, wherein the packaging solution comprises a polyionic material and at least one hydrolysable-at-autoclave material, wherein the polyionic material includes (i) a polymer having a hydrophobic backbone and multiple charged or ionizable pendant groups, (ii) a chitosan, or (iii) a combination thereof, wherein the packaging solution has an initial pH of less than about 4.0, wherein the hydrolysable-at-autoclave material is present in the packaging solution in an amount sufficient to impart a final neutral pH to the packaging solution after the package with the contact lens therein is autoclaved;
   (b) sealing the lens package with the contact lens and the packaging solution having the initial pH of less than about 4.0 therein; and
   (c) autoclaving said sealed package with the contact lens and the packaging solution therein, thereby hydrolyzing the hydrolysable-at-autoclave material and imparting the final neutral pH to the packaging solution in the sealed package, wherein the LbL coating has a hydrophilicity characterized by an averaged water contact angle of about 80 degrees or less.

2. The method of claim 1, wherein the polyionic material includes a polyanionic material having a hydrophobic backbone and pendant ionizable groups, and wherein the hydrolysable-at-autoclave material is urea, ammonium carbamate, or combination thereof.

3. The method of claim 2, wherein the polyanionic material comprises carboxyl groups.

4. The method of claim 2, wherein the polyanionic material is a linear or branched polyacrylic acid, or a linear or branched acrylic acid copolymer.

5. The method of claim 4, wherein the packaging solution further comprises a polycationic material.

6. The method of claim 5, wherein the concentration of the polyanionic material is at least 2 folder higher than that of the polycationic material.

7. The method of claim 4, wherein the packaging solution further comprises a non-charged hydrophilic material with a hydrophobic backbone, wherein the non-charged hydrophilic material is a polyvinyl alcohol, a homopolymer of a vinyl lactam, a copolymer of at least one vinyl lactam in the presence or in the absence of one or more hydrophilic vinylic comonomers, or a mixture thereof.

8. The method of claim 7, wherein the non-charged hydrophilic material is a polyvinyl alcohol, a homopolymer of a vinyl lactam, a copolymer of at least one vinyl lactam in the presence or in the absence of one or more hydrophilic vinylic comonomers, or a mixture thereof.

9. The method of claim 4, wherein the packaging solution further comprises a chitosan.

10. The method of claim 1, wherein the polyionic material includes a chitosan, and wherein the hydrolysable-at-autoclave material is urea, ammonium carbamate, or combination thereof.

* * * * *